United States Patent [19]
Loomis et al.

[11] Patent Number: 6,004,287
[45] Date of Patent: Dec. 21, 1999

[54] BIOLISTIC APPARATUS FOR DELIVERING SUBSTANCES INTO CELLS AND TISSUES

[76] Inventors: Dale J Loomis, 334 S. George Rd., Freeville, N.Y. 13068; Joe Celeste, 3411 Rte. 414, Burdett, N.Y. 14819; John Sanford, 43 Sunset Dr., Geneva, N.Y. 14456

[21] Appl. No.: 09/158,816

[22] Filed: Sep. 23, 1998

Related U.S. Application Data

[60] Provisional application No. 60/059,771, Sep. 23, 1997.

[51] Int. Cl.⁶ .................................................. A61M 11/00
[52] U.S. Cl. ............................................. 604/68; 604/141
[58] Field of Search ................................. 604/68, 69, 70, 604/71, 151, 152, 140, 141, 143

[56] References Cited

U.S. PATENT DOCUMENTS

| | | | |
|---|---|---|---|
| 5,569,190 | 10/1996 | D'Antonio | 604/68 X |
| 5,599,302 | 2/1997 | Lilley et al. | 604/68 |
| 5,851,198 | 12/1998 | Castellano et al. | 604/68 |
| 5,919,159 | 7/1999 | Lilley et al. | 604/68 |

*Primary Examiner*—John D. Yaskos
*Attorney, Agent, or Firm*—Sughrue, Mion, Zinn, Macpeak & Seas, PLLC

[57] ABSTRACT

A biolistic apparatus is provided with a housing having a carrier membrane disposed in a chamber for movement relative to an outlet plate having a plurality of apertures therein. The carrier membrane has a plurality of microparticles adhered thereto on the surface of the membrane adjacent the apertures for delivery into cells or tissue. A plurality of rupturable membranes are mounted in spaced relation to the carrier membrane. Initially, a vacuum is provided within the assembly including the outlet opening to purge the apparatus of any undesirable gasses. High pressure helium is then delivered to the rupturable membranes and upon reaching a predetermined pressure, will cause the membranes to rupture allowing a shock front of high pressure helium to strike the carrier membrane and impel the articles through the outlet openings.

6 Claims, 7 Drawing Sheets

FIG. 24 ns
BIOLISTIC APPARATUS FOR DELIVERING SUBSTANCES INTO CELLS AND TISSUES

RELATED APPLICATION

Applicants claim priority benefits of provisional application 60/059,771 filed Sep. 23, 1997 under 35 USC 119(e).

BACKGROUND OF THE INVENTION

The present invention is directed to a biolistic device for accelerating micro-projectiles into intact cells or tissues. More specifically, the present invention is directed to a biolistic device having a gas shock generator for applying a gas shock to a fixed carrier membrane to distend the membrane and separate micro-projectiles from the surface of the membrane at high speeds into the target cells or tissues.

For medical applications, a biolistic device must have several characteristics including safety, reproducibility, ease of use, non-trauma for the patient and minimal injury to the bombarded tissue. At the same time, maximum particle dispersion, maximum particle velocity and maximal skin penetration are needed. Existing biolistic devices need improvement in terms of delivery, efficacy, reproducibility, gentleness and ease of use. Many of the prior art devices make a loud noise which can be frightening and impact the skin with a violent shock wave of helium gas. Prior art configurations utilizing a "flying disk" has shot to shot variation and subjects the skin to a violent shock wave and does not achieve as much dispersal or penetration as might be desired.

SUMMARY OF THE INVENTION

The present invention provides a new and improved biolistic apparatus for injecting particles into cells and tissues which is extremely safe, easy to use, highly reproducible, makes essentially no noise, is painless and causes minimal trauma to the bombarded skin.

The device according to the present invention has been shown to result in better particle dispersal, deeper skin penetration and higher subsequent biological activities.

The present invention provides a new and improved biolistic device which effectively but gently accelerates micro-projectiles into intact cells or tissues such as skin comprising a gas shock generator, a fixed malleable membrane between the gas shock and the target, a shaped stopping surface disposed between the fixed membrane and the target for controlled deceleration of the distending membrane and apertures in the stopping surface which allow the transport of high speed micro-projectiles from the surface of the fixed membrane into the target.

The present invention provides a new and improved biolistic device for accelerating micro-projectiles into intact cells or tissues which utilizes a gas shock generator comprised of a plurality of burst membranes which are clamped together upon initial application of pressure and will substantially, simultaneously burst when the pressure applied thereto reaches a predetermined value thereby releasing the gas under pressure substantially instantaneously to create a shock wave for contacting a carrier membrane and impaling the micro-particles thereon into a target.

The present invention provides a new and improved biolistic device for accelerating micro-projectiles into intact cells or tissues comprising a gas shock generator including a magnetically controlled valve which is held shut by magnetic force until pressure being applied thereto is sufficient to break the magnetic seal at which point the magnetic seal suddenly collapses and the valve opens whereby a shock wave is projected against a deformable carrier membrane to impel the micro-particles thereon into the cells or tissues.

The above and other objects, features and advantages of the present invention will be more apparent and more readily appreciated from the following detailed description of preferred exemplary embodiment of the present invention, taken in connection with the accompanying drawings.

DETAILED DESCRIPTION OF THE INVENTION

Figure 1:
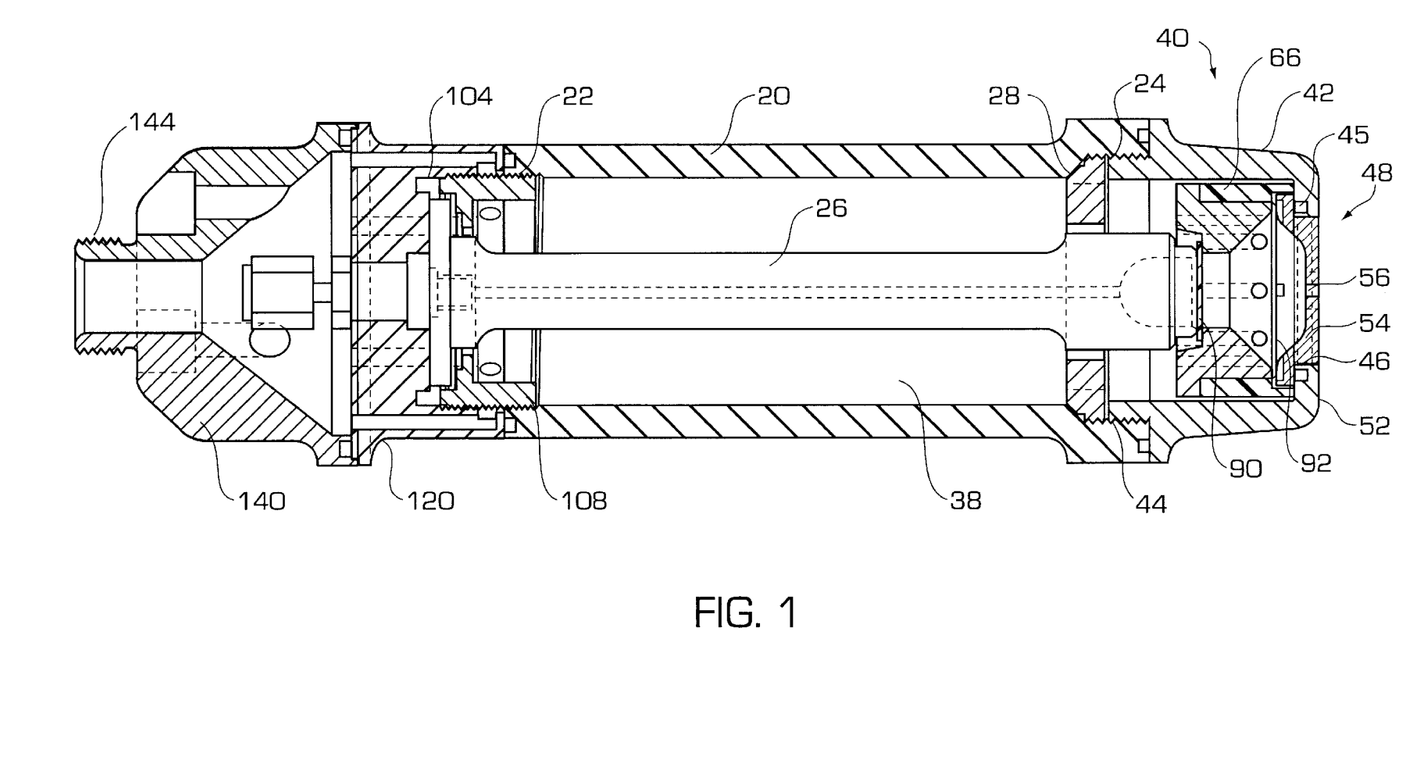
FIG. 1 is a side elevation view of a biolistic device, partly in section and partly broken away, for accelerating micro-projectiles into intact cells or tissues.
Figure 2:
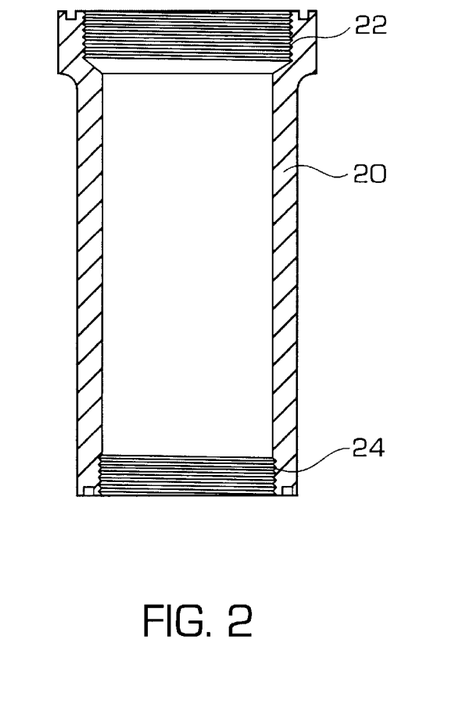
FIG. 2 is a sectional view of the housing of the device shown in FIG. 1.
Figure 3:
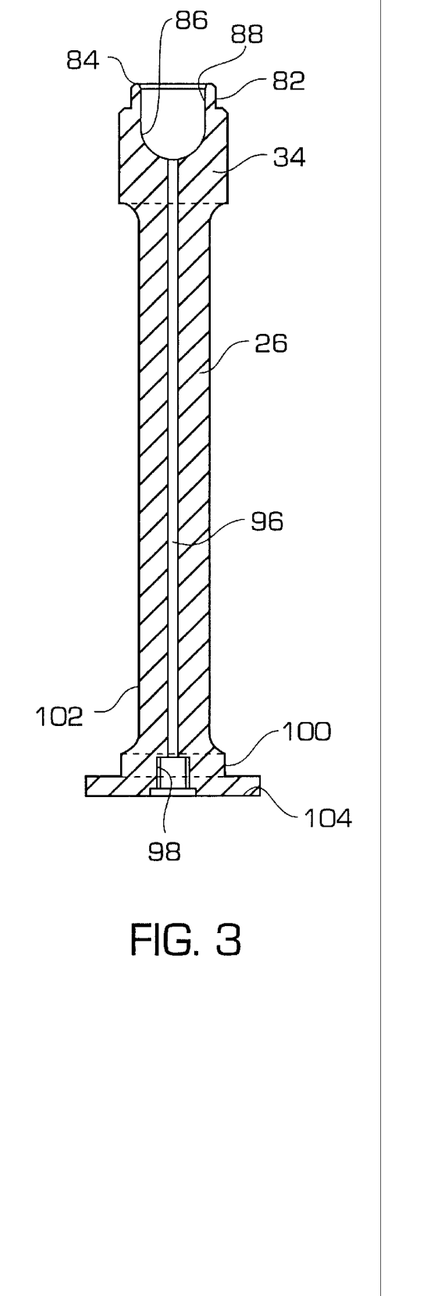
FIG. 3 is a sectional view of the piston assembly which extends through said housing in concentric relation thereto.
Figure 4:
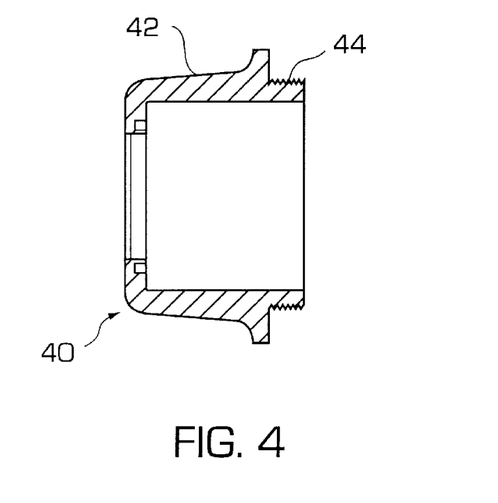
FIG. 4 is a sectional view of the nozzle body as shown in FIG. 1.
Figure 5:
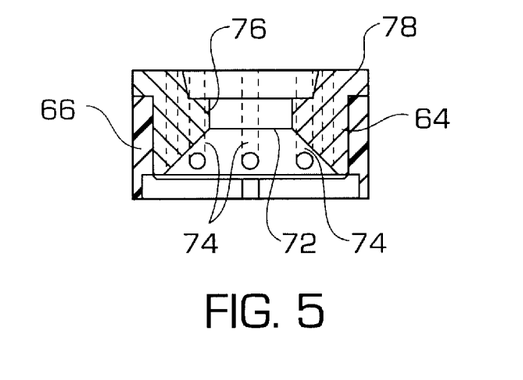
FIG. 5 is a sectional view of the coupler shown in FIG. 1 between the burstible membranes and the carrier membrane with gas flow passages shown in phantom lines.
Figure 6:
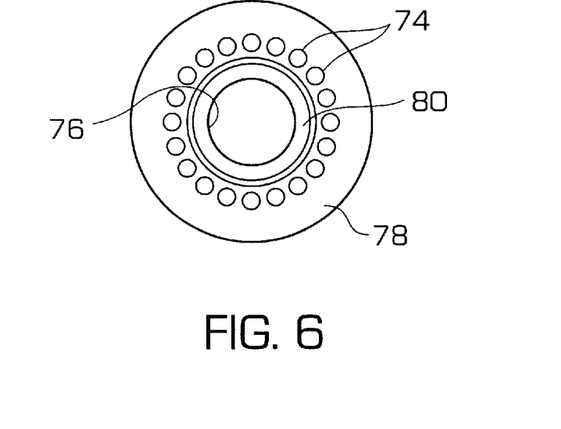
FIG. 6 is a rear end view of the coupler shown in FIG. 5.
Figure 7:
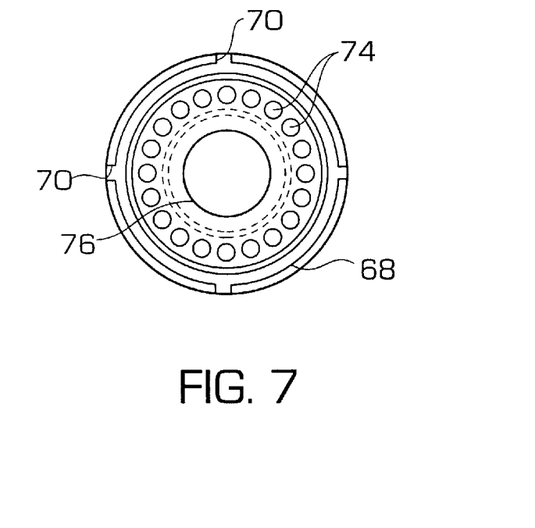
FIG. 7 is a front end view of the coupler shown in FIG. 5.
Figure 8:
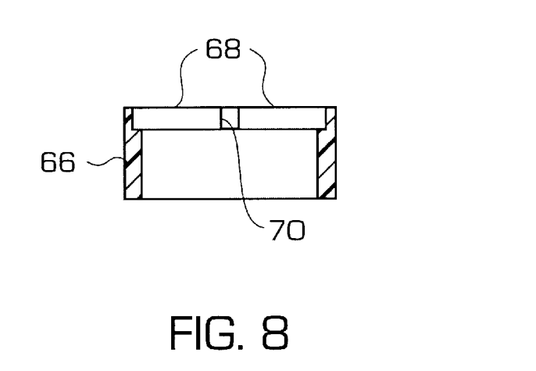
FIG. 8 is a sectional view of a supporting ring for the coupler as shown in FIG. 1.
Figure 9:
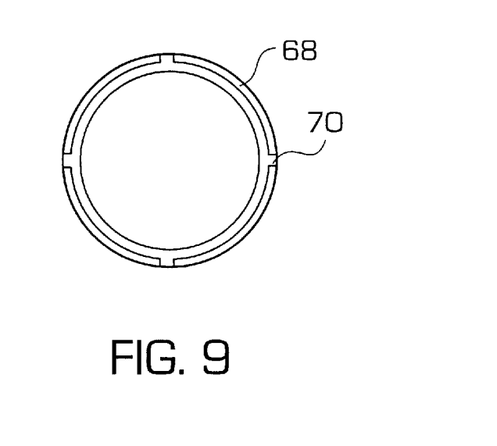
FIG. 9 is a front end view of the support ring as shown in FIG. 8.
Figure 10:
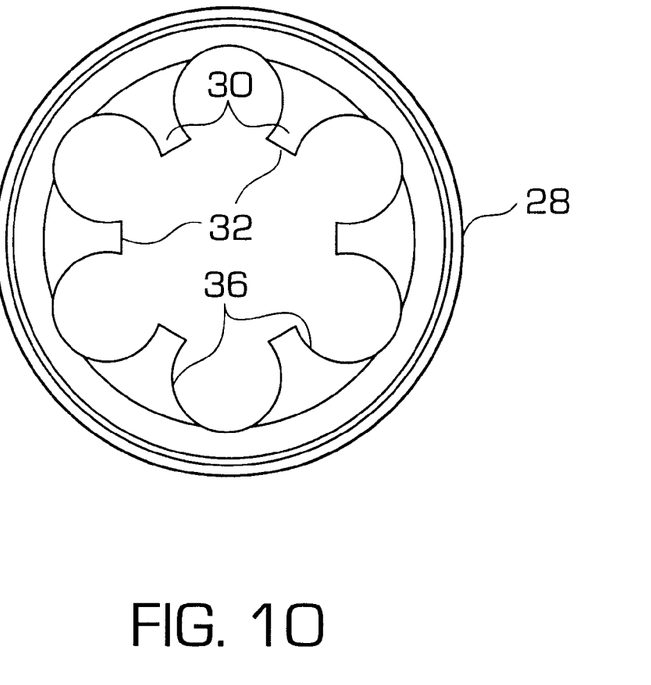
FIG. 10 is an end view of a support ring for supporting the forward end of the piston assembly.
Figure 11:
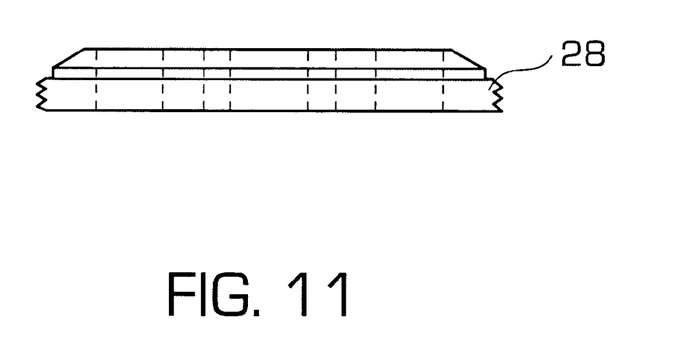
FIG. 11 is a side elevation view of the support ring shown in FIG. 10.
Figure 12:
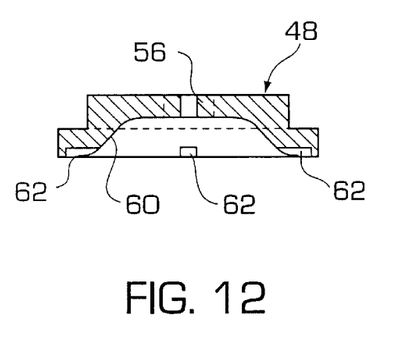
FIG. 12 is a sectional view of the nozzle outlet plate as shown in FIG. 1.
Figure 13:
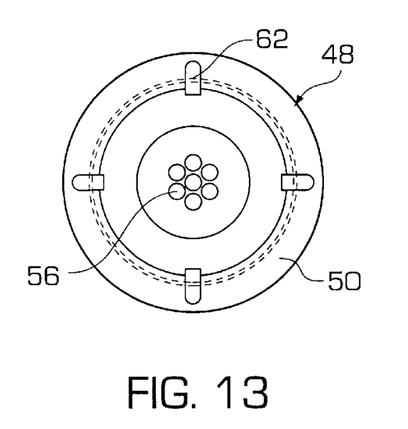
FIG. 13 is a rear elevational view thereof.
Figure 14:
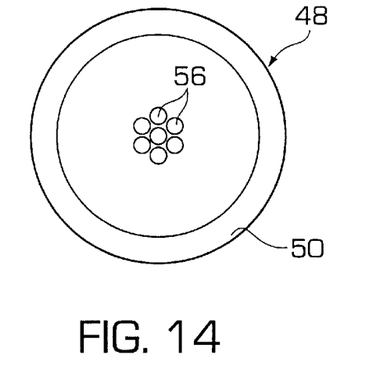
FIG. 14 is a front elevational view thereof.
Figure 15:
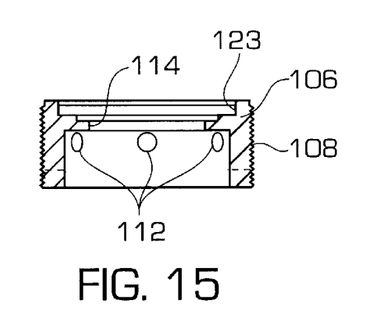
FIG. 15 is a sectional view of the retaining ring secured in the opposite end of the housing from the nozzle body.
Figure 16:
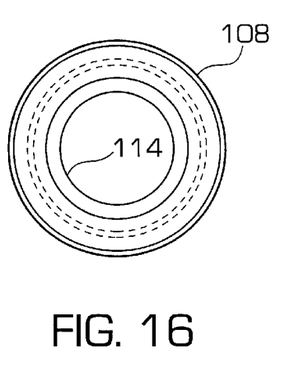
FIG. 16 is a rear elevational view thereof.
Figure 17:
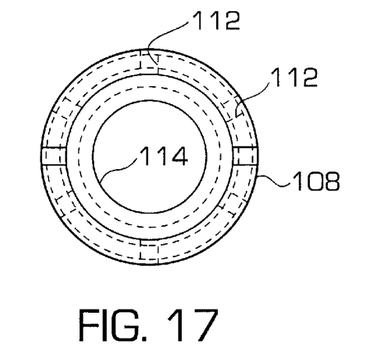
FIG. 17 is a front elevational view thereof.
Figure 18:
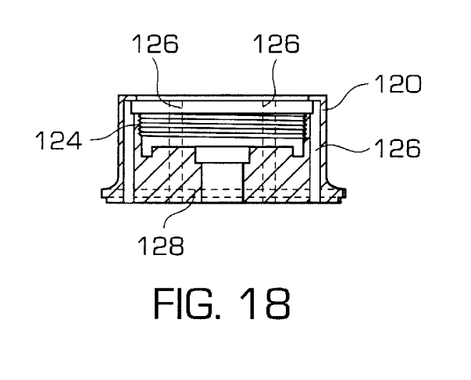
FIG. 18 is a sectional view of the pressure chamber secured to the retainer ring at the rear end of the housing.
Figure 19:
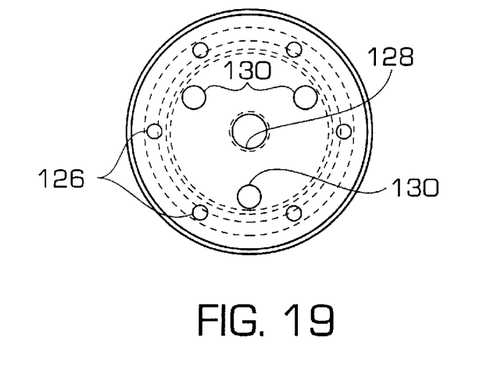
FIG. 19 is a rear elevational view thereof.
Figure 20:
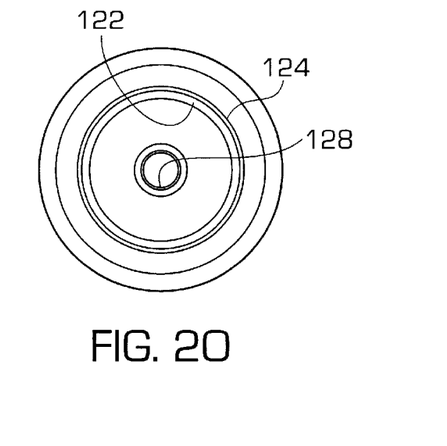
FIG. 20 is a front elevational view thereof.
Figure 21:
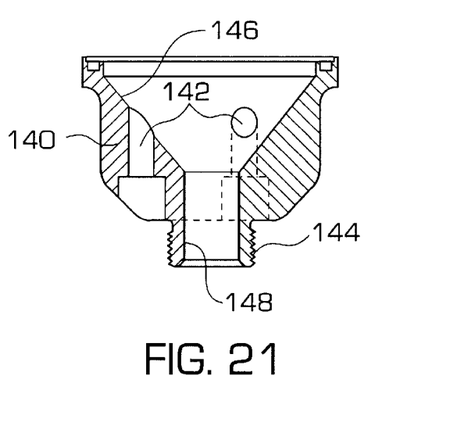
FIG. 21 is a sectional view of the end cap secured to the pressure chamber member.
Figure 22:
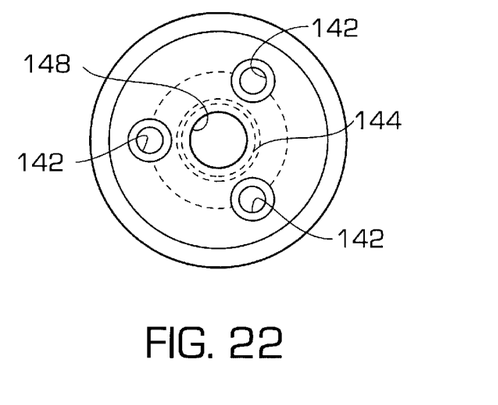
FIG. 22 is a rear elevational view thereof.
Figure 23:
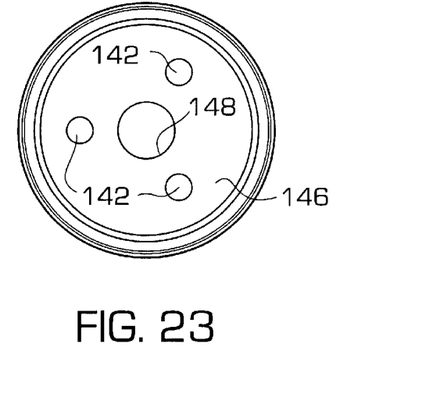
FIG. 23 is a front elevational view thereof.
Figure 24:
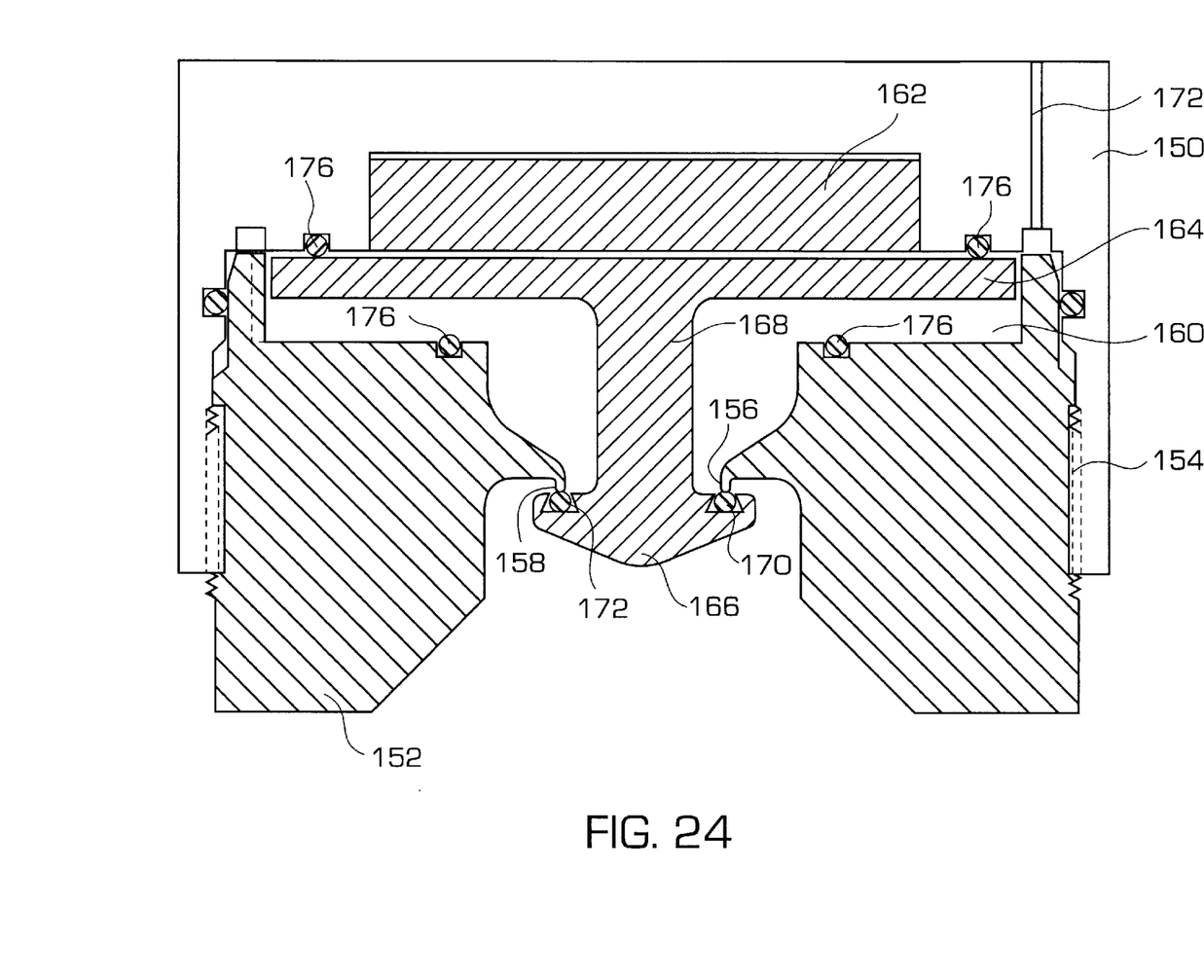
FIG. 24 is a sectional view of a magnetically controlled gas pressure valve according to a second embodiment of the invention.

The apparatus of the present invention is shown in assembled form in FIG. 1 and is comprised of a hollow, cylindrical housing 20 having internal threads 22 and 24 at opposite ends thereof. An elongated piston assembly 26 is mounted in the hollow, cylindrical housing 20 concentrically thereof. The piston assembly 26 is supported at its forward end by means of an annular member 28 (FIG. 10) disposed in threaded engagement with the threads 24 of the housing. The annular member 28 is provided with a plurality of radially, inwardly directed projections 30 having inner ends 32 disposed on a circle having a diameter equal to the diameter of the pressure chamber 34 at the forward end of the piston assembly. A plurality of cut out portions 36 are located between each projection 30 to provide communication between the annular chamber 38 located between the piston assembly 26 and the housing 20 and the interior of the nozzle assembly 40.

The nozzle assembly 40 (FIGS. 4–9 and 14) is comprised of a nozzle body 42 having an externally threaded hub portion 44 disposed in threaded engagement with the threads 24 at the forward end of the housing 20. The opposite end of the nozzle body 42 is provided with a circular opening 46 which receives a nozzle outlet plate 48. The nozzle outlet plate 48 is provided with a larger diameter flange portion 50 adapted to engage the internal surface of an annular flange 52 formed on the nozzle body 42. A smaller diameter central portion 54 having a plurality of through passages 56 is located within the opening 46 in the end of the nozzle body 42. An 0 ring 58 is disposed in a groove on the internal face of the flange 52 to seal the nozzle outlet plate to the nozzle body 42. The internal surface of the nozzle outlet plate 48 is provided with a recess 60 and the flange 50 is provided with four grooves 62 equally spaced apart.

An annular coupler 64 is mounted in the nozzle body adjacent the nozzle outlet plate 48 by means of an annular ring 66 of delrin material. The forward end of the support ring 66 is provided with four axially extending flange portions 68 equally spaced about the circumference of the ring to define gaps 70 therebetween. The forward end of the coupler 64 is provided with a recess 72 having a trapezoidal cross section with the smaller base of the trapezoid having a diameter equal to the diameter of the axially extending central passage 76 of the coupler 64. A plurality of axially extending bores 74 are equally spaced about the central passage 76 to provide communication between the recess 72 and the rearward surface of the coupler.

The rearward surface 78 of the coupler is provided with an enlarged recess 80 which is concentric with the axial bore 76 extending through the coupler. The pressure chamber 34 of the piston assembly 26 is provided with a forwardly extending flange 82 with an annular crown 84 on the forward end thereof. The flange 82 is dimensioned to closely fit within the recess 80 in the coupler member. The pressure chamber portion 34 is provided with a substantially hemispherical pressure chamber 86 which merges into a cylindrical passage 88 extending through the flange 82 and having a diameter identical to the diameter of the bore 76 extending through the coupler 64. A plurality of kapton membranes 90 having an external diameter substantially equal to the diameter of the recess 80 in the coupler, are disposed in the recess 80 for engagement by the crown 84 on the forward end of the flange 82 on the pressure chamber member 34. The number of membranes 90 may vary depending upon the desired strength since the plurality of membranes are adapted to burst when the desired pressure is reached in the pressure chamber 86. A single stronger carrier membrane 92 having a diameter equal to the diameter of the nozzle outlet plate flange 50 is disposed between the flange 50 and the coupler with sufficient play to allow communication between the through passages 56, the recessed portion 60, the recessed portion 72 and the annular chamber 38 in the absence of pressure being applied to the membrane 92 in the forward direction.

The piston assembly 26 has an axially extending bore 96 extending the full length of the piston assembly in communication with the pressure chamber 86 and a cylindrical recess 98 at the opposite end thereof. The piston assembly 26 is provided with a cylindrical hub portion 100 having a larger diameter than the elongated body 102 of the piston assembly. At the end of the piston assembly, an enlarged flange 104 is provided adjacent the hub portion 100.

Adjacent the rearward end of the housing 20, a retaining ring 106 having external threads 108 thereon, is threaded into engagement with the internal threads 22 of the housing 20. The retaining ring 106 is provided with an axially extending recess 110 at the forward end thereof having a plurality of radially directed passages 112 extending outwardly to the threads 108. The retaining ring 106 is also provided with a reduced diameter bore 114 in which the hub portion 100 of the piston assembly 26 is slidably mounted. A pressure chamber member 120 is provided with a forwardly extending recess 122 having an internally threaded portion 124 which is threaded onto the external threads of the retaining ring 106. The enlarged diameter end portion 104 of the piston assembly 26 is disposed in a recess 123 in the rearward portion of the retaining ring 1–6 and is exposed to pressure in the recess 122 of the pressure chamber member. The pressure chamber member 120 is also provided with a plurality of through bores 126 disposed adjacent the periphery of the pressure member 120. A central bore 128 is provided for introducing pressure into the pressure chamber and a plurality of threaded passages 130 are provided about the central bore 128 for the reception of connecting members.

An end cap 140 is secured to the rearward end of the pressure chamber member 120 by means of cap screws (not shown) extending through three bores 142 which are in alignment with the threaded passages 130 in the pressure chamber member. The rear end of the end cap is provided with an externally threaded nozzle 144 which is adapted to be connected to a suitable vacuum source and a high pressure helium source (not shown). The end cap is provided with a recess 146 in the forward end thereof having a trapezoidal cross section with the recess in communication with the inlet passage 148 extending through the nozzle 144.

In the operation of the apparatus according to the present invention, the forward end of the nozzle body 40 is pressed against the tissue to be inoculated with particles such as genetic material. Since the forward surface of the nozzle outlet plate 54 is recessed relative to the nozzle body as best seen in FIG. 1, a thin chamber is formed in communication with the passages 56 through which the particles are ejected. A vacuum is applied to the entire assembly by connecting the nozzle 144 to a suitable vacuum source through valve means (not shown). The vacuum is applied through the axial passage 148 of the nozzle 144, the recess 146 in the end cap and the annular chamber 38 by means of the connecting passages 126. The vacuum is also applied to the passages 56 in the outlet plate 54 as well as the outer surface of the outlet plate 54 through the recess 60 in the outlet plate 48, the passages 74 extending through the coupler 64 to the annular chamber 38 through the openings 36 in the annular support member 28, Since the carrier membrane 92 is mounted with sufficient play, it is possible for the vacuum to be applied around the periphery of the carrier membrane through the grooves 62 in the flange of the outlet plate. By applying the vacuum to the system, the atmospheric gasses, as well as any residual helium gasses from a previous usage, are removed from the vacuum body as well as removing any stray gas from the high pressure chamber and the lines supplying the accelerator. Thus, during a subsequent ejection operation, only helium gas will be in the high pressure chamber 86 rather than the usual mix of air and helium gas.

After sufficient vacuum is introduced, a vacuum sensor (not shown) will initiate the introduction of pressurized helium gas through the nozzle 144. The pressurized helium gas will act on the enlarged end portion 104 of the piston assembly 26 to shift the piston assembly 26 axially to bring the crown 84 on the flange 82 of the piston assembly 26 into clamping engagement with the burst membranes 90 by clamping the burst membranes 90 against the bottom of the enlarged recess 80 in the rear surface of the coupler. The pressurized helium gas will also enter through the recess 98 in the rearward end of the piston assembly and the elongated through passage 26 to the pressure chamber 86. The pressure will ramp up in the high pressure chamber 86 until it reaches the yield pressure of the burst membranes 90. The membrane system can consist of any desired number of membranes. For example, the membrane system may consist of 4.002" (2 mil) kapton membranes or disks. Each disk would have a burst pressure of approximately 400 psi. As the pressure reaches the yield point of the kapton group, one of the membranes will burst, rapidly followed by the second, third and fourth. When the fourth membrane yields, the pressure against it is four times its burst point.

The gas chamber or high pressure chamber 86 is designed to allow an energy efficient gas front to reach the captivated membrane. The gas chamber is designed with a length to width (aspect ratio) of approximately 1:1. The spherical rear shape of the high pressure chamber recovers some of the energy lost when the membranes initially yield. The length of the chamber is optimized to create the most efficient pressure front with the least amount of excess gas. This allows a smaller vacuum body to be designed, as less total volume of helium gas has to be controlled. As the pressure front advances, it accelerates the captive carrier membrane which is also made of kapton material. The carrier membrane is halted abruptly as it stops against the flange of the outlet plate and closes the grooves 62. The particles adhered to the surface of the carrier membranes, such as generic material, leave the carrier membrane as it suddenly deforms into the recess 60 and fly through the holes in the stopping plate to enter the target tissue. The recess 60 in the nozzle outlet plate 48 allows the carrier membrane to deform outwardly without rupturing. However, under certain circumstances, it may be desirable to have the carrier membrane also rupture.

By containing the carrier membrane in tact, the force of the gas blast will not reach the tissue, thereby eliminating pressure trauma to the tissue. Force of the high pressure helium can be dissipated rearwardly through the passages 74 in the coupler into the large annular chamber 38, which is still under vacuum.

The actual flight distance of the carrier membrane is reduced from many centimeters in prior art structures to far less than one centimeter and the target is disposed in substantially intimate contact with the stopping plate. The carrier membrane 90 acts as a one way valve inasmuch as it previously allowed a vacuum to be introduced to the target but which is sealed against the outlet plate to prevent the gas front from getting in front of the carrier membrane and disrupting the flight characteristics of the genetic material.

According to a second embodiment of the present invention, a magnetically controlled valve may be utilized in lieu of the rupturable membranes of the first embodiment whereby repeatability can be enhanced without the need for replacing the ruptured membranes. The valve, as shown in FIG. 24, would still be used with the carrier membrane as shown in the previous embodiment.

A housing 150 is provided with a recess having a valve body 152 secured therein by means of a threaded connection 154. The valve body 152 is provided with a valve opening 156 having an annular valve seat 158 extending outwardly from a valve chamber 160 defined between the housing and the valve body. A neodymium magnet 162 is mounted in a recess in the housing 150 with a major surface thereof exposed to the interior of the valve chamber 160. An iron or steel plunger 164 is mounted in the valve chamber 160 and is provided with a stem 168 which extends through the valve opening 156 and is provided with an enlarged head 166. An O ring 170 having a diameter equal to the diameter of the valve seat 158 is mounted in a groove 172 having a trapezoidal cross section to assist in retaining the O ring within the groove under stressful conditions.

In operation, the plunger is drawn into engagement with the magnet, whereby the O ring will be moved into sealing engagement with the valve seat. High pressure gas is introduced into the valve chamber through a gas line 172. The high pressure gas fills the valve chamber 160 in contact with opposite surfaces of the main body of the plunger and upon reaching a predetermined pressure, will cause the plunger to separate from the magnet. Once the plunger leaves contact with the magnet, the holding force will be substantially reduced and the plunger will move downwardly as viewed in FIG. 24 to release the gas within the chamber with an explosive force creating a shock wave which will strike the carrier membrane to inject the particles adhering to the opposite surface of the membrane into cells or tissue. Once the pressure drops within the valve chamber 160, the force of the magnet will retract the plunger into contact with the magnet and seal the valve opening by means of the O ring 170. Suitable bumpers 176 are provided on opposite sides of the plunger plate to cushion the impact of the plunger plate against the housing and the valve body.

The entire disclosure of the provisional application upon which priority is claimed, is hereby incorporated into the present application by reference.

While the invention has been particularly shown and described with reference to preferred embodiments thereof, it will be understood by those in the art that the foregoing and other changes in form and details may be made therein without departing from the spirit and scope of the invention.

What is claimed is:

1. An apparatus for delivering micro-projectiles into cells or tissue comprising:

a hollow cylindrical housing, a nozzle assembly secured to one end of said housing and including a plate having a plurality of through passages, an annular ring slidably mounted in said nozzle, a carrier membrane for carrying micro-projectiles disposed between said annular ring and said plate, a piston coaxially disposed in said housing in radial spaced relation thereto and having a central bore extending coaxially through said piston, one end of said piston having a pressure chamber therein and a flange disposed about said chamber, support means mounting said piston for axial sliding movement relative to said housing, a plurality of burst membranes disposed between said flange and said annular ring, an opposite end of said piston having a radially extending flange, pressure means for applying pressure to said flange for moving said piston to clamp said burst membranes against said ring and for applying pressure to said burst membranes whereby upon rupture of said burst membranes a surge of high pressure will engage said carrier membrane to impel said micro-projectiles outwardly of said nozzle assembly through said passage in said plate.

2. An apparatus as set forth in claim 1, wherein said carrier membrane is mounted for movement relative to said plate, said plate having a peripheral flange with a plurality of radially extending grooves whereby upon application of pressure to said carrier membrane said carrier membrane will be moved into engagement with said flange to close said grooves.

3. An apparatus as set forth in claim 2, further comprising a plurality of axially extending passages in said annular ring disposed in communication with said grooves in said plate in the absence of pressure being applied to said carrier membrane and disposed in communication with an annular space between said housing and said piston and means for connecting said annular space to a vacuum source to provide a vacuum in said passages of said plate when said nozzle assembly is disposed in contact with tissue.

4. An apparatus as set forth in claim 3, further comprising an end cap secured to an opposite end of said housing and having vacuum and pressure connecting means therein.

5. An apparatus as set forth in claim 1, wherein said pressure chamber in said one end of said piston has a length to width ratio of approximately 1:1 and is provided with a substantially hemispherical configuration.

6. A biolistic device which effectively but gently accelerates micro-projectiles into intact cells or tissues such as skin comprising:

a gas shock generator, a fixed, malleable membrane between the gas shock and the target, a shaped stopping surfaced for controlled de-acceleration of the distending membrane, immediately separating the fixed membrane and the target, and apertures in the stopping surface which allow transport of high speed micro-projectiles from the surface of the fixed membrane into the target.

* * * * *